(12) United States Patent
Uhara et al.

(10) Patent No.: US 7,253,309 B2
(45) Date of Patent: Aug. 7, 2007

(54) METHOD FOR PRODUCTION OF METHACRYLIC ACID

(75) Inventors: Hiroyuki Uhara, Tatsuno (JP); Kazuo Anyouji, Himeji (JP); Hideyuki Hironaka, Himeji (JP); Hideo Onodera, Himeji (JP)

(73) Assignee: Nippon Shokubai Co., Ltd, Osaka-shi, Osaka (JP)

( * ) Notice: Subject to any disclaimer, the term of this patent is extended or adjusted under 35 U.S.C. 154(b) by 0 days.

(21) Appl. No.: 10/353,528

(22) Filed: Jan. 29, 2003

(65) Prior Publication Data

US 2003/0162997 A1 Aug. 28, 2003

(30) Foreign Application Priority Data

Feb. 7, 2002 (JP) .............................. 2002-030890

(51) Int. Cl.
*C07C 51/235* (2006.01)
*C07C 51/16* (2006.01)

(52) U.S. Cl. ................... 562/532; 562/524; 562/545

(58) Field of Classification Search ............... 562/400, 562/512, 517, 518, 523, 531, 532
See application file for complete search history.

(56) References Cited

U.S. PATENT DOCUMENTS 3,516,800 A   6/1970  Yamamoto et al.
4,273,676 A *  6/1981  Matsumoto et al. ........ 502/209
4,803,302 A   2/1989  Oh-Kita et al.
5,153,162 A  10/1992  Kurimoto et al.
5,191,116 A   3/1993  Yamamatsu et al.
5,211,929 A   5/1993  Durand et al.
5,276,178 A   1/1994  Onodera et al.
6,410,786 B1  6/2002  Onodera et al.
2001/0024630 A1*  9/2001  Matsumoto et al. ........ 422/201
2004/0171874 A1  9/2004  Watanabe et al.

FOREIGN PATENT DOCUMENTS

EP   0 421 875 A1   10/1990
EP   1 166 865 A2   4/2001
JP   60012134        1/1985
JP   A-5-96172       4/1993
JP   A-6-86932       3/1994
JP   A-7-163883      6/1995

* cited by examiner

*Primary Examiner*—Karl Puttlitz
(74) *Attorney, Agent, or Firm*—Mathews, Shepherd, McKay & Bruneau, P.A.

(57) ABSTRACT

This invention is related to a shell-and-tube type reactor provided with reaction tubes packed with a catalyst and adapted to circulate a heat medium to the fluid outside the tubes and is characterized by a method introducing a gas into the catalyst beds so as to retain the relative humidity of the catalyst in the range of more than 40% while elevating the temperature of the reactor thereby starting up the reactor. This method prevents the catalyst from degradation of activity due to absorption of moisture, exalts the service life of the catalyst, and permits stable production of methacrylic acid.

4 Claims, No Drawings

METHOD FOR PRODUCTION OF METHACRYLIC ACID

BACKGROUND OF THE INVENTION

1. Field of the Invention

This invention relates to a method for the production of methacrylic acid and more particularly to a method for the production of methacrylic acid, which includes a step of starting up a reactor by introducing therein a preheated gas so as to retain the relative humidity of the catalyst bed not more than 40% while elevating the temperature of the reactor.

2. Description of the Related Art

Methacrylic acid is the raw material for a general-purpose resin which demands quantity production. Heretofore, it has been known to adopt for the production of methacrylic acid a method using a shell-and-tube type reactor which has incorporated therein built-in reaction tubes packed with an oxidizing catalyst. The official gazette of JP-A-04-90853, for example, discloses a method for the production of methacrylic acid, which is characterized by using a methacrylic acid-producing catalyst containing at least the oxygen compounds of phosphorus and molybdenum. The official gazette of JP-A-2001-11010 discloses a method for producing methacrylic acid by effecting the gas phase catalytic oxidation of methacrolein with a fixed-bed shell-and-tube type reactor, which method comprises using a molybdovanadophosphoric acid complex oxide as a catalyst and requiring the reaction tubes to be packed with the catalyst in such a manner that the quantity of the catalytically active component per unit volume of the reaction tubes may decrease from the raw material gas inlet part toward the outlet part.

Methacrylic acid is produced by the oxidation and/or oxidodehydrogenation of at least one compound selected from among methacrolein, isobutyl aldehyde, isobutyric acid, and isobutane. This reaction is exothermic in kind. For the purpose of recovering the heat of this reaction, therefore, it is necessary to circulate a heat medium to the reactor. Since the solidifying point of the heat medium generally is so high as to fall in the range of 50-250° C., the production of methacrylic acid with a reactor which is left standing at room temperature necessitates adoption of a specific method of starting up the reactor. The official gazette of JP-A-2001-310123, for example, discloses as a means of starting up a reactor adapted to circulate such a heat medium, a method which effects quick startup of the reactor by introducing a gas heated to a temperature in the range of 100-400° C. to the reaction tubes' side thereby starting elevation of the temperature of the reaction tubes, then circulating a heated heat medium to the fluid outside the reaction tubes, and introducing a gas of an elevated temperature in advance to the reaction tubes thereby preventing the heat medium which has been circulated from being re-solidified.

Since methacrylic acid is the raw material for a general-purpose resin, it is required to have the production efficiency thereof further improved by exalting the conversion ratio and the selectivity of the raw material compound. Further, methacrylic acid is a compound which is produced by continuously feeding the raw material gas and operating the plant for a long time. Thus, it is required to develop the development a method for improving the service life of a catalyst for use in the production line thereby exalting the productivity of the pertinent operation and stabilizing the production of methacrylic acid for a long time.

SUMMARY OF THE INVENTION

The present inventor, as a result of performing a study concerning the method for producing methacrylic acid by using a shell-and-tube type reactor incorporating reaction tubes packed with a catalyst, has discovered that the catalyst for use in the production of methacrylic acid, on absorbing moisture, suffers the catalytic activity thereof to be lowered, that the catalyst tends to induce absorption of moisture anew during the startup of the shell-and-tube type reactor, and that, by introducing a preheated gas so as to adjust the relative humidity of a catalyst bed to a level of not more than 40% while elevating the temperature of the reactor thereby starting up the reactor, it is made possible to prevent the catalyst from yielding to the degradation of quality due to the absorption of moisture and enable the catalyst to induce stable production of methacrylic acid in high yields. This invention has been perfected as a result.

Specifically, this invention is aimed at attaining stable production of methacrylic acid in high yields for a long time by introducing a preheated gas into a shell-and-tube type reactor incorporating reaction tubes packed with a catalyst in order to adjust the relative humidity of the catalyst beds to a level of not more than 40% and elevating the temperature of the preheated gas as to start up the reactor thereby preventing the catalyst beds from absorbing moisture and preventing the catalytic activity from being degraded by absorption of moisture. This invention is particularly effective when the catalyst comprises a heteropoly acid in order to use for the production of methacrylic acid. The raw material compound for methacrylic acid is the gas containing at least one compound selected from among methacrolein, isobutyl aldehyde, isobutyric acid, and isobutane. The invention manifests an excellent effect when the raw material gas is subjected in the gas phase to oxidation and/or oxidodehydrogenation with molecular oxygen or a gas containing molecular oxygen.

According to this invention, by supplying a preheated gas adapted to adjust the relative humidity of the catalyst beds to a level of not more than 40% in starting up the reactor, it is made possible to prevent the catalyst from absorbing moisture and from yielding to degradation of the catalytic activity and enhance the yield of methacrylic acid. The activation of the catalyst results in not merely enhancing the conversion ratio of the raw material compound and the selectivity of the product aimed at but also lowering the reaction temperature and consequently attaining stable maintenance of the catalytic activity over a long period.

DESCRIPTION OF THE PREFERRED EMBODIMENTS

This invention concerns a method for producing methacrylic acid by using a shell-and-tube type reactor incorporating reaction tubes packed with a catalyst and circulating a heat medium as a fluid outside the reaction tubes, which method comprises introducing a preheated gas adapted to retain the relative humidity of the catalyst beds in the range of not more than 40% while elevating the temperature of the preheated gas thereby starting up the reactor and preventing the catalyst from absorbing moisture.

The method for producing methacrylic acid by using a shell-and-tube type reactor generally effects the production by introducing a raw material gas and an oxidizing gas into reaction tubes packed with the catalyst and subjecting the raw material gas to the reaction of catalytic gas phase oxidation at a reaction temperature in the range of 200-500°

C. A heteropoly acid type catalyst is counted among the oxidizing catalysts which are used in this reaction. This catalyst is a compound which is liable to absorb moisture and, on absorbing moisture, suffers degradation of catalytic activity through a change in crystal structure. Generally, after the reaction tubes have been packed with the catalyst, they are sealed in the upper and lower parts thereof for the purpose of preventing the catalyst therein from absorbing moisture. The absorption of moisture by the catalyst occurs anew, however, during the process of producing methacrylic acid, particularly during the startup of the reactor, and induces degradation of the catalytic activity. It has been found that the catalyst beds wet with the absorbed moisture can be dried afterward by introducing a preheated gas of a high temperature but the catalytic activity once lowered can never be recovered. Now, this invention will be described.

The reaction for the synthesis of methacrylic acid is an exothermic reaction. For the purpose of continuing the operation of the reactor while controlling the reaction temperature of the catalyst with which the reaction tubes are packed, the heat medium is supplied to the outside of the reaction tubes and made to absorb heat and the heat medium is cooled outside the reactor and then circulated into the reactor. A fused salt is counted among the heat media which are usable in this case. The solidifying point of such a fused salt is generally in the range of 50-250° C. In starting up the reactor, the inside and the outside of the reactor are both at normal room temperature. For the purpose of introducing the thermal medium into the reactor while preventing the heat medium from yielding to solidification, therefore, it is necessary to preheat the reaction tubes before the heated heat medium is introduced into the reactor. The heat medium being introduced into the reactor is prevented from solidification by introducing the preheated gas into the reaction tubes and heating the reaction tubes from the inside. When the heat medium already introduced into the reactor is left cooling after the production aimed at is completed, the heat medium solidified remains in the reactor. When the reactor in the state is to be put to use again, it is necessary to introduce the preheated gas into the reaction tubes and heat the reaction tubes from inside so as to enable the heat medium in the reactor to ensure fluidity. In any event, for the purpose of starting up the reactor, the practice of introducing the preheated gas into the reaction tubes packed with the catalyst thereby melting the heat medium and enabling it to ensure fluidity and, in consequence of the heating, enabling the catalyst to retain the activity thereof is generally followed.

It is the inexpensive air that is generally used as the preheated gas in this case. When the humid air in the atmosphere is preheated in its undried state, the exposure of the catalyst beds to the preheated air results in suffering the catalyst to absorb the moisture of the air. Since the heteropoly acid which is favorably used as a catalyst for the production of methacrylic acid exhibits high hygroscopicity, it suffers the salt structure thereof to be partly transformed to an acid form thereof by absorbing moisture. In the heteropoly acid type catalyst which exhibits an excellent quality in the production of methacrylic acid, for example, the Keggin structure as a basic skeleton thereof forms a salt structure. This catalyst, on absorbing moisture, suffers this structure to deform. This deformed structure is not reverted even when the wet catalyst is subsequently dried and the catalytic activity once degraded remains in its degraded state. This invention, therefore, has decided to start up the reactor by introducing the preheating gas into the catalyst beds starting up the reactor so as to adjust the relative humidity of the catalyst beds to a level of not more than 40%, preferably not more than 30%, and particularly preferably not more than 20% while elevating the temperature of the catalyst. It is inferred that the salt structure is not altered and the degradation of the quality of the catalyst is repressed because this adjustment of the relative humidity results in restraining the absorption of moisture by the catalyst. Though the effect of this adjustment is heightened in accordance as the magnitude of relative humidity is lowered, it is economical for the elimination of the moisture from the gas to set this magnitude at a level of not more than 40% which suffices to obtain a satisfactory effect. This invention, however, is not restricted by this theoretical discussion.

The relative humidity of the catalyst bed contemplated by this invention can be calculated by the water content in the preheated gas and the temperature of the catalyst bed. To be specific, the ratio (%) of the weight of the steam contained in a fixed volume of the gas (Y) (Pa/m$^3$) to the quantity of the saturated steam of that gas (the maximum weight of the steam that can be contained at the relevant temperature) ($Y_s$) (Pa/m$^3$) is adopted as the relative humidity ($100 \times Y/Y_s$). The temperature of the catalyst bed can be found from a thermometer (thermocouple) inserted in advance into the catalyst bed formed in a given reaction tube and the water content of the preheated gas can be determined by sampling the preheated gas being introduced into the reaction tube and measuring the water content of the sample. The relative humidity of the catalyst beds can be calculated by using the numerical values so obtained. Though the temperature of the catalyst bed may well be regarded as equaling the temperature of the reactor, it can be possibly varied by the temperature of the heat medium introduced into the reactor and the temperature of the ambient air.

Now, the method according to this invention for the production of methacrylic acid will be described more specifically below.

The shell-and-tube type reactor to be used in this invention does not need to be particularly restricted but may be arbitrarily selected from among the known reactors which satisfy the requirements of incorporating reaction tubes packed with a catalyst and allowing circulation of a heat medium outside the reaction tubes with the object of absorbing the heat of reaction generated within the reaction tubes. Generally, the reactor has tube sheets disposed one each at the top and the bottom of the shell thereof and adapted to hold in place a plurality of reaction tubes by their opposite terminals and also has an inlet and an outlet formed in the shell thereof for the fluid circulated outside the reaction tubes with the object of eliminating the heat generated in there action tubes. The reactor may have one or more interior sheet in order to divide the reactor into a plurality of chambers and may have the reaction tubes in the different chambers packed with catalysts differing in kind.

The catalyst which fills the reaction tubes is a catalyst intended for use in the production of methacrylic acid. It catalyzes the reaction of oxidation for converting the —CHO contained in methacrolein or isobutyl aldehyde into —COOH, the reaction of oxidation for converting one of the —CH$_3$'s contained in isobutane into —COOH, or the reaction of oxidodehydrogenation of converting CH$_3$—CH< into CH$_2$=C<. A heteropoly acid type catalyst containing phosphorus and molybdenum may be cited as one concrete example.

As a concrete example of the heteropoly acid type catalyst which catalyzes the reaction of oxidation or the reaction of oxidodehydrogenation mentioned above, a catalyst which contains a molybdovanadophosphoric acid represented by the formula, $Mo_aP_bA_cB_dC_eO_x$ (wherein Mo stands for molybdenum, P for phosphorus, A for at least one element selected from among arsenic, antimony, germanium, bismuth, zirconium, selenium, cerium, copper, iron, chromium, nickel, manganese, cobalt, tin, silver, zinc, palladium, rhodium, and tellurium, B for at least one element selected from among vanadium, tungsten, and niobium, C for at least one element selected from among alkali metals, alkaline earth metals, and thallium, O for oxygen, and a, b, c, d, e, and x stand for such numbers respectively of the atoms Mo, P, A, B, C, and O as satisfy b=0.5–4, c=0.001–5, d=0.001–4, e=0.001–4, and x=the numerical value to be automatically determined by the states of oxidation of the relevant elements where a=12 is assumed) may be cited. Other concrete examples include the catalyst for use in the production of methacrylic acid which contains at least the oxides of phosphorus, molybdenum, vanadium, iron, copper, and antimony as disclosed in the official gazette of JP-A-62-161739, the catalyst for use in the production of methacrylic acid which contains at least the oxides of phosphorus and molybdenum as disclosed in the official gazette of JP-A-04-90853, the multicomponent type catalyst for use in the production of methacrylic acid which contains phosphorus, molybdenum, vanadium, and copper as disclosed in the official gazette of JP-A-05-96172, the catalyst for use in the production of methacrylic acid which contains at least the oxides of phosphorus, molybdenum, vanadium, and arsenic as disclosed in the official gazette of JP-A-06-86932, and the catalyst for use in the production of methacrylic acid which contains at least the oxides of molybdenum, phosphorus, vanadium, antimony, rhenium, and sulfur as disclosed in the official gazette of JP-A-07-163883. These catalysts do not need to be particularly discriminated on account of shape and size. They may assume such shapes as spheres, circular columns, and cylinders, for example. The catalyst to be used in this invention does not need to be particularly restricted with respect to the method of production and the kind of raw material. The method and the raw material which have been heretofore used generally in the preparation of a catalyst of this kind may be used. For the purpose of preventing the produced catalyst from absorbing moisture, the catalyst is preferred to be preserved in a sealed container till it is put to use.

The method for packing the reaction tubes with the catalyst does not need to be particularly restricted. The packing may be carried out by any of the ordinary methods which are available. Incidentally, since this invention is aimed at preventing the catalyst from absorbing moisture, the reaction tubes which have been packed with the catalyst are preferred to be sealed at the top and the bottom so as to avoid exposing the catalyst to the atmosphere.

The preheated gas to be introduced into the reaction tubes does not need to be particularly restricted but is only required to avoid exerting any influences even when it is mixed with the catalyst packed in the reaction tubes or with the raw material gas. Thus, air and such inert gases as carbon dioxide, nitrogen gas, and argon gas may be favorably used for the preheated gas, though variably depending on the kind of the catalyst for filling the reaction tubes and the kind of the raw material gas to be supplied.

The heat medium does not need to be particularly restricted excepting the solidifying point thereof which is only required to be in the range of 50-250° C. The catalysts which have such solidifying points include organic heat media, molten salt (niter), and molten metal, for example. Among other heat media which are used for controlling the temperatures of the chemical reactions, the niter is particularly at an advantage in exhibiting excellent thermal stability and retaining the highest stability in the heat exchange performed at such high temperatures as 350-550° C. The niter is the so-called molten salt which forms a varying composition and manifests a varying solidifying point as well. For this invention, the niter can be advantageously used so long as it possesses the solidifying point mentioned above without reference to the form of composition. The compounds which are used for the niters of this class include sodium nitrate, sodium nitrite, and potassium nitrate. They may be used either singly or in the form of a combination of two or more members. In this invention, the preheated gas which has the temperature thereof elevated with a heater to a level in the range of 50-400° C. is introduced with a blower into the reaction tubes which have been packed with the catalyst necessary for the production of methacrylic acid. The gas is led out of the reactor through any one terminal on the upper tube sheet side or the lower tube side of the reaction tubes. By the introduction of the preheated gas, the interior of the reactor is enabled to have the temperature thereof elevated from the reaction tubes' side. In this case, for the purpose of introducing the preheated gas into the catalyst beds so as to set the relative humidity of the catalyst bed to a level of not more than 40%, it is advantageous to use the gas dehumidified in advance only after it has been treated with a heat exchanger. The origin of the preheated gas to be introduced into the reaction tubes is irrelevant. The preheated gas which has occurred from some apparatus facility other than the apparatus used in the process for production of methacrylic acid and the preheated gas which has been dehumidified at such other apparatus may be used. It is economical to use the preheated gas which has been dehumidified in a refrigerator in the process mentioned above. When the temperature of the catalyst beds is such that the dehumidification with the refrigerator in the process mentioned above is incapable of lowering the relative humidity of the catalyst beds to a level not more than 40%, such an external dehumidified gas as, for example, the air spent for the instrumentation may be independently used. It is also permissible to use the dehumidified air so obtained as mixed with the air which has been dehumidified with the refrigerator in the process for the production of methacrylic acid.

The relative humidity of the catalyst beds in this invention is varied by the water content in the preheated gas and the temperature of the catalyst beds as described above. When the water content in the preheated gas is fixed, therefore, the trend of the preheated gas toward formation of frost grows in proportion as the temperature of the catalyst beds decreases. The relative humidity of the catalyst beds rises to the highest level during the start of the introduction of the preheated gas into the reactor. If the water content in the preheated gas does not vary, the relative humidity of the catalyst beds decreases in proportion as the temperature of the catalyst beds rises. For the purpose of elevating the temperature of the preheated gas while keeping the relative humidity of the catalyst beds not more than 40%, therefore, it is advantageous to use the preheated gas of a low water content during the initial state of the introduction. Once the catalyst beds are heated to a temperature of about 100° C., the relative humidity of the catalyst beds can be lowered to a level of not more than 40% by switching the dehumidified gas to the ordinary air or to the combustion gas obtained by subjecting the exhaust component from the process of production to combustion. When the air is used as the preheated gas and the temperature of the catalyst beds is not higher than 100° C., this air is put to use after it has been humidified.

So long as the temperature of the catalyst beds is high, the relative humidity of the catalyst beds can be easily lowered to a level of not higher than 40% even when the water content of the preheated gas is high. When the temperature of the catalyst beds adjusted to a level in the range of 50-60° C. by introducing the heated heat medium into the reactor, the air dehumidified only to a low degree may be heated and put to use.

To produce methacrylic acid in accordance with this invention, the temperature of the catalyst beds is elevated, after this temperature has reached a level in the range of 200-500° C., the reaction of oxidation and/or the reaction of oxidodehydrogenation is started by the method described above. In the place of the preheated gas mentioned above, the raw material gas, the oxidizing gas such as molecular oxygen or a molecular oxygen-containing gas, and the inert gas such as carbon dioxide, nitrogen gas, or argon gas, namely the gases which have been heretofore introduced into the shell-and-tube type reactor for the production of methacrylic acid, are introduced. Air is a typical oxygen-containing gas. It is economic to use air as the gas for this introduction. As the raw material gas to be introduced, the gas which contains at least one compound selected from among methacrolein, isobutyl aldehyde, isobutyric acid, and isobutane is available. Depending on the kind and the composition of a catalyst to be used, the introduction of methacrolein results in producing methacrylic acid by the reaction of oxidation, the introduction of isobutyl aldehyde and/or isobutane results in producing methacrylic acid by the reaction of oxidation and the reaction of oxidodehydrogenation, and the introduction of isobutyric acid results in producing methacrylic acid by the reaction of oxidodehydrogenation.

This invention does not impose any particular restriction on the conditions for the reaction of oxidation or on the conditions for the reaction of oxidodehydrogenation. These reactions can be carried out under the conditions which are in common use. The reaction is satisfactorily effected by forwarding 1-10 vol. %, preferably 2-8 vol. %, of the raw material compound formed of at least one member selected from the group consisting of methacrolein, isobutyl aldehyde, isobutyric acid, and isoburane and 2-20 vol. %, preferably 3-20 vol. %, of a mixed gas composed of molecular oxygen and an inert gas such as steam, nitrogen, or carbon dioxide at a temperature in the range of 200-500° C., preferably 250-450° C., under a pressure in the range of $1 \times 10^5$-$1 \times 10^6$ Pa, preferably $1 \times 10^5$-$8 \times 10^5$ Pa, at a space velocity in the range of 100-5,000 $hr^{-1}$ (STP), preferably 500-4,000 $hr^{-1}$ (STP) to contact with the catalyst. By preventing the catalyst from absorbing moisture according to this invention, it is made possible to improve the conversion ratio of the raw material compound such as methacrolein or isobutyric acid and the selectivity of the product aimed at and increase the yield of methacrylic acid. When isobutyl aldehyde is adopted as the raw material, since the activity of the oxidizing reaction is improved, the selectivity of methacrylic acid is heightened particularly for the fixed reaction temperature and the yield of methacrylic acid is finally improved. As is clearly noted from the working examples described herein below, by adopting the startup which precludes the catalyst from absorbing moisture, it is made possible to attain repression of the reaction temperature to a low level while allowing the selectivity and the conversion ratio to be heightened, prevent the catalyst from being deteriorated by heat, and permit stable production of methacrylic acid to be continued for a long time.

Since methacrolein can be produced from isobutylene, t-butanol, or methyl-t-butyl ether, the production of methacrylic acid may be attained by preparatorily deriving a methacrolein-containing gas from such a compound, adopting this gas as the raw material gas mentioned above, and introducing this raw material gas into the catalyst beds. The use of such a methacrolein-containing gas is especially commendable in respect that it obviates the necessity for purification in the commercial process. As the oxidizing catalyst for the production of methacrolein from isobutylene, for example, the catalyst containing a complex oxide which is represented by the formula, $Mo_aW_bBi_cFe_dA_eB_fC_gD_hE_iO_x$ (wherein Mo stands for molybdenum, W for tungsten, Bi for bismuth, Fe for ion, A for one element selected from nickel and cobalt, B for one element selected from alkali metals and thallium, C for one element selected from alkaline earth metals, D for at least one element selected from phosphorus, tellurium, antimony, tin, cerium, lead, niobium, manganese, arsenic, and zinc, E for at least one element selected from silicon, aluminum, titanium, and zirconium, and O for oxygen, and a, b, c, d, e, f, g, h, i, and x stand for such numbers respectively of the atoms Mo, W, Bi, Fe, A, B, C, D, E, and O as satisfy b=0-10, c=0.1-10, d=0.1-20, e=2-20, f=0-10, g=0.001-10, h=0-4, i=0-30, and x=the numerical value automatically determined by the states of oxidation of the relevant elements where a=12 is assumed) disclosed in the official gazette of JP-A-09-194409. Since the niter is used as the heat medium in the shell-and-tube type reactor also in the production of methacrolein with this reactor, it is only common to introduce a preheated gas into the reactor. Since the complex oxide catalyst mentioned above rarely induces degradation of the activity of the catalyst due to moisture absorption, it has only a bare necessity for elevating the temperature thereof while restraining the relative humidity of the catalyst beds below 40%. Meanwhile, when the reactor is divided into two chambers, an upper one and a lower one, with at least one interior sheet, it may be operated for producing methacrylic acid while using the chamber packed with the aforementioned complex oxide catalyst on the isobutylene-containing gas supplying side and the other chamber packed with the aforementioned heteropoly acid type catalyst. In this case, since the heteropoly acid type catalyst mentioned above possesses hygroscopicity, the absorption of moisture by the catalyst beds and the degradation of the activity thereof can be prevented by starting up the reactor by the elevation of the temperature thereof while retaining the relative humidity of the catalyst beds not more than 40% owing to the supply of a preheated gas. While isobutylene is used herein as the raw material gas, the embodiment of the use of this raw material gas is embraced by the scope of this invention because it is made to produce methacrolein by the complex oxide catalyst represented by the aforementioned formula, $Mo_aW_bBi_cFe_dA_eB_fC_gD_hE_iO_x$, and this methacrolein is made to produce methacrylic acid by the aforementioned heteropoly acid type catalyst.

When two reactors are used together, for example, the first reactor packed with the composite oxide catalyst may be operated to produce a methacrolein-containing gas from isobutylene and then the second reactor packed with the heteropoly acid type catalyst may be operated to produce methacrylic acid from the methacrolein-containing gas. The methacrolein-containing gas can be used without being limited to what is obtained by the reaction of catalytic gas phase oxidation of isobutylene.

Experiments

Now, this invention will be described more specifically below with reference to working examples. This invention is not restricted by these working examples. The conversion ratio, selectivity, and per-pass yield are defined as follows.

Conversion ratio(%)=[(Number of moles of reacted raw material compound)/(Number of moles of supplied raw material compound)]×100

Selectivity (%)=[(Number of moles of formed methacrylic acid)/(Number of moles of reacted raw material compound)]×100

Per-pass yield (%)=[(Number of moles of formed methacrylic acid)/(Number of moles of supplied raw material compound)]×100

EXAMPLE 1

(Startup of Reactor)

A shelled monotubular reaction tube measuring 25 mm in inside diameter and 4 m in length was charged with 1.3 L. of a catalyst for the production of methacrylic acid (containing a heteropoly acid and having a composition of $P_{1.3}Mo_{12}V_{0.8}Cs_{1.2}Cu_{0.2}Zr_{0.1}$). The temperature of the catalyst bed consequently formed was 30° C.

To this reaction tube, a preheated gas obtained by preparing air dehumidified with a refrigerator to a water content of 1.47 vol. % and heating this air to 130° C. was introduced at a flow rate of 15 L. per minute. The relative humidity of the catalyst bed at the time of starting the introduction of the preheated gas was 35% (Startup 1)).

(Oxidizing Reaction)

A mixed gas containing 3.5 vol. % of methacrolein, 8.5 vol. % of oxygen, and 15 vol. % of steam and obtained by catalytic gas phase oxidation of isobutylene in the presence of a molybdenum-bismuth-iron-cobalt multicomponent type composite oxide catalyst was introduced into this reactor and subjected to the reaction of oxidation at a reaction temperature of 280° C. and a space velocity of 1100 $hr^{-1}$ (STP). The results are shown in Table 1.

COMPARATIVE EXAMPLE 1

(Startup of Reactor)

The startup was made by following the procedure of Example 1 while omitting the dehumidification of air with the refrigerator. The water content of the preheated gas was 2.51 vol. % and the relative humidity of the catalyst bed at the time of starting the introduction of the preheated gas was 60% (Startup 2).

(Oxidizing Reaction)

The reaction of oxidation was carried out by following the procedure of Example 1 while changing the startup of the reactor from (Startup 1) to (Startup 2) and changing the reaction temperature to 288° C. The results are shown in Table 1.

EXAMPLE 2

(Startup of Reactor)

The operation was performed by following the procedure of Example 1 while setting the temperature of the catalyst in the reaction tube at 53° C. by introducing a heated heat medium into the reactor and introducing air having water content of 2.51 vol. % as a preheated gas into the catalyst bed. The relative humidity of the catalyst bed at the time of starting the introduction of the preheated gas was 18% (Startup 3).

(Oxidizing Reaction)

Methacrylic acid was obtained by the reaction of oxidation performed by following the procedure of Example 1 while changing the startup of the reactor from (Startup 1) to (Startup 3). The results are shown in Table 1.

EXAMPLE 3

(Startup of Reactor)

The reactor was started up by following the procedure of Example 1 while allowing the completed catalyst bed to acquire a temperature of 25° C. and introducing into the reaction tube a preheated gas (water content 0.53 vol. %) prepared by mixing air with the air for instrumentation and heating the resultant mixture. The relative humidity of the catalyst bed at the time of starting the introduction of the preheated gas was 17% (Startup 4).

(Oxidizing Reaction)

Methacrylic acid was obtained by the reaction of oxidation performed by following the procedure of Example 1 while changing the startup of the reactor from (Startup 1) to (Startup 4). The results are shown in Table 1.

COMPARATIVE EXAMPLE 2

(Startup of Reactor)

The startup was carried out by following the procedure of Example 1 while allowing the completed catalyst bed to acquire a temperature of 22° C. The relative humidity of the catalyst bed at the time of starting the introduction of the preheated gas was 56% (Startup 5).

(Oxidizing Reaction)

Methacrylic acid was obtained by the reaction of oxidation performed by following the procedure of Example 1 while changing the startup of the reactor from (Startup 1) to (Startup 5) and changing the reaction temperature to 287° C. The results are shown in Table 1.

TABLE 1

| | RH of catalyst bed (%) | Reaction temp. (° C.) | Conversion ratio of meth-acrolein (mole %) | Selectivity of meth-acrylic acid (mole %) | Per-pass yield of meth-acrylic acid (mole %) |
|---|---|---|---|---|---|
| Example 1 | 35 | 280 | 83.4 | 82.5 | 68.8 |
| Comparative Example 1 | 60 | 288 | 82.3 | 80.8 | 66.5 |
| Example 2 | 18 | 280 | 86.8 | 81.5 | 70.7 |
| Example 3 | 17 | 280 | 87.1 | 81.3 | 70.8 |
| Comparative Example 2 | 56 | 287 | 82.7 | 80.9 | 66.9 |

RH: Relative humidity

Results: From the results of Examples 1-3 and Comparative Examples 1 and 2, it is seen that the method of this invention could prevent degradation of catalytic activity by precluding the decline of catalytic activity. By comparing Example 1 and Comparative Example 1, it is noted that Example 1 which started up the reactor with the relative humidity of the catalyst bed set below 35% showed a higher conversion ratio of methacrolein and a higher selectivity of methacrylic acid than Comparative Example 1, excelled in catalytic quality, and enjoyed an improved per-pass yield of methacrylic acid. From Examples 1-3, it is seen that the conversion ratio of methacrolein and the selectivity of methacrylic acid were both increased and the per-pass yield of methacrylic acid was improved in proportion as the relative humidity of the catalyst bed was lowered. From Examples 1-3 and Comparative Example 1 and 2, it is seen that when the startup was made while the relative humidity of the catalyst bed was in a high state as in the comparative examples, the same catalytic activity as obtained in the working examples could not be obtained even when the reaction temperature of the catalyst bed was high.

EXAMPLE 4

The oxidizing reaction was continued over a period of 4000 hours by following the procedure of Example 1. The results at the end of the 4000 hours' reaction are shown in Table 2.

COMPARATIVE EXAMPLE 3

The oxidizing reaction was continued over a period of 4000 hours by following the procedure of Comparative Example 1. The results at the end of the 4000 hours' reaction are shown in Table 2.

TABLE 2

|  | RH of catalyst bed (%) | Reaction temp. (° C.) | Conversion ratio of meth-acrolein (mole %) | Selectivity of meth-acrylic acid (mole %) | Per-pass yield of meth-acrylic acid (mole %) | Remark |
|---|---|---|---|---|---|---|
| Example 4 | 35 | 284 | 83.2 | 82.8 | 68.9 | After 4000 hours |
| Comparative Example 3 | 60 | 297 | 82.7 | 80.8 | 66.8 | After 4000 hours |

RH: Relative humidity

Results: By comparing Example 4 and Comparative Example 3, it is found that Example 4 which started up the reactor with the relative humidity of the catalyst bed set at 35% maintained the conversion ratio of methacrolien and the selectivity of methacrylic acid both at high levels even after the elapse of 4000 hours, enjoyed a long service life of catalyst, and continued a stable oxidizing reaction for a long time, notwithstanding it had a lower reaction temperature than Comparative Example 3.

EXAMPLE 5

The oxidizing reaction was carried out by following the procedure of Example 1 while introducing a mixed gas containing 3.5 vol. % of isobutyl aldehyde, 10 vol. % of oxygen, and 10 vol. % of steam as the raw material gas for use in the oxidizing reaction and changing the space velocity of the raw material gas to 900 hr$^{-1}$. The results are shown in Table 3.

COMPARATIVE EXAMPLE 4

The oxidizing reaction was carried out by following the procedure of Example 5 while changing the startup of the reactor from (Startup 1) to (Startup 2). The results are shown in Table 3.

TABLE 3

|  | RH of catalyst bed (%) | Reaction temp. (° C.) | Conversion ratio of isobutyl aldehyde (mole %) | Selectivity of meth-acrolein (mole %) | Selectivity of meth-acrylic acid (mole %) | Per-pass yield of meth-acrylic acid (mole %) |
|---|---|---|---|---|---|---|
| Example 5 | 35 | 280 | 100 | 12.1 | 66.1 | 66.1 |
| Comparative Example 4 | 60 | 280 | 100 | 15.0 | 63.3 | 63.3 |

RH: Relative humidity

Results: The mechanism of the reaction for deriving methacrylic acid from isobutyl aldehyde is considered as proceeding from isobutyl aldehyde and terminating in formation of methacrylic acid via methacrolein. Example 5 and Comparative Example 4 were not different in the efficiency of reaction from isobutyl aldehyde to methacrolein because they both showed a conversion ratio, 100 mole %, of isobutyl aldehyde. Example 5 which made the startup with the relative humidity of the catalyst bed set at 35%, however, showed an increase of 2.8 mole % in the selectivity of methacrylic acid and an increase of 2.8 mole % in the per-pass yield of methacrylic acid as compared with Comparative Example 4. The selectivity of methacrolein was 12.1 mole % in Example 5 and 15.0 mole % in Comparative example 4. In spite of the lower selectivity of methacrolein, Example 5 showed a higher per-pass yield of methacrylic acid than Comparative Example 4 probably because Comparative Example 4 had an inferior efficiency of the reaction for transforming methacrolein to methacrylic acid and a high ratio of unaltered methacrolein.

EXAMPLE 6

The reaction was carried out by following the procedure of Example 1 while using a mixed gas containing 3.5 vol. % of isobutyric acid, 9 vol. % of oxygen, and 10 vol. % of steam as the raw material gas for the reaction and changing the space velocity to 1200 $hr^{-1}$. The results are shown in Table 4.

COMPARATIVE EXAMPLE 5

The oxidizing reaction was carried out by following the procedure of Example 5 while changing the startup of the reactor from (Startup 1) to (Startup 2). The results are shown in Table 4.

TABLE 4

|  | RH of catalyst bed (%) | Reaction temp. (° C.) | Conversion ratio of isobutyric acid (mole %) | Selectivity of methacrylic acid (mole %) | Per-pass yield of methacrylic acid (mole %) |
|---|---|---|---|---|---|
| Example 6 | 35 | 280 | 99.1 | 79.1 | 78.4 |
| Comparative Example 5 | 60 | 280 | 96.7 | 77.8 | 75.2 |

RH: Relative humidity

Results: Example 6 showed a higher conversion ratio of isobutyric acid and a higher selectivity than Comparative Example 5 and thus indicated excellence in catalytic activity. The fact that the selectivity of isobutyric was high means that the ratio of the reaction of oxidodehydrogenation of isobutyric acid into methacrylic acid was high. From the results of Example 6 coupled with those of Example 5, it is seen that for the fixed relative humidity, 35%, of the catalyst bed, changes in the raw material compound brought increases in the activity of oxidodehydrogenation as compared with the comparative example.

The invention claimed is:

1. A method for the production of methacrylic acid by the use of a shell-and-tube type reactor incorporating built-in reaction tubes packed with a heteropoly-acid catalyst and circulating a heat medium as a fluid outside the reaction tubes, said method comprises dehumidifying and heating air prior to introduction to said catalyst, introducing said preheated and dehumidified air into catalyst beds to maintain the relative humidity of the catalyst beds in the range of not more than 40% while elevating the temperature of said reactor thereby starting up the reactor, and preventing the catalyst from absorbing moisture and, introducing a gas containing at least one compound selected from the group consisting of methacrolein, isobutyl aldehyde, isobutyric acid, and isobutene to said catalyst beds to oxidize and/or oxidodehydrogenate at least one compound selected from said group consisting of methacrolein, isobutyl aldehyde, isobutyric acid, and isobutene in a gas phase with molecular oxygen or a molecular oxygen-containing gas thereby obtaining said methacrylic acid.

2. A method according to claim 1, wherein said preheated and dehumidified air is first dehumidified and then treated with a heat exchanger prior to being introduced into the catalyst beds.

3. A method according to claim 1, wherein the relative humidity of the catalyst beds is not more than 30%.

4. A method according to claim 2, wherein the relative humidity of the catalyst beds is not more than 30%.

* * * * *

UNITED STATES PATENT AND TRADEMARK OFFICE
CERTIFICATE OF CORRECTION

| | | |
|---|---|---|
| PATENT NO. | : 7,253,309 B2 | Page 1 of 1 |
| APPLICATION NO. | : 10/353528 | |
| DATED | : August 7, 2007 | |
| INVENTOR(S) | : Hiroyuki Uhara et al. | |

It is certified that error appears in the above-identified patent and that said Letters Patent is hereby corrected as shown below:

The Title Page (73) should read as follows:

SUMITOMO CHEMICAL CO., LTD., Chuo-ku, Tokyo (JP)

Signed and Sealed this

Twenty-seventh Day of November, 2007

JON W. DUDAS
*Director of the United States Patent and Trademark Office*